May 11, 1954 H. J. McREYNOLDS ET AL Plant Pat. 1,276

GRAPEFRUIT TREE

Filed Dec. 23, 1952

Hudson J. McReynolds,
Oliver L. Peacock,
by Royal E. Burnham,
Attorney.

Patented May 11, 1954 Plant Pat. 1,276

UNITED STATES PATENT OFFICE 1,276

GRAPEFRUIT TREE

Hudson J. McReynolds, Orlando, and Oliver L. Peacock, Fort Pierce, Fla.

Application December 23, 1952, Serial No. 327,708

1 Claim. (Cl. 47—62)

The present discovery relates to a new and distinct variety of grapefruit tree, originating as a bud sport of the well-known pink Marsh seedless tree, unpatented.

The new variety was discovered as a sport by us, during the fruit season 1943–1944, in a cultivated grove of approximately 2,400 grapefruit trees owned by one of us, Hudson J. McReynolds, located in Saint Lucie County, Florida, on the east side of the Header Canal, approximately twelve miles west of the city of Fort Pierce, and about two miles north of the Fort Pierce-Okeechobee highway. The distinctive fruit of the new variety is exemplified in the accompanying drawing, of which—

Figure 1:
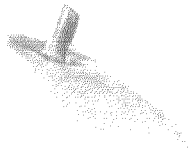
Fig. 1 is an exterior view of one of the fruit.
Figure 2:
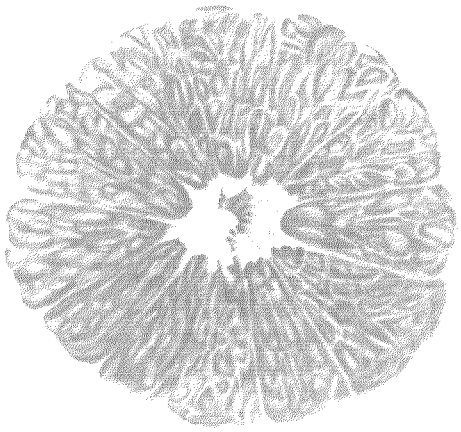
Fig. 2 is a transverse mid section in a plane substantially perpendicular to the axis of the fruit.

A distinctive feature of the fruit of our tree is that the flesh of the fruit is of several reddish hues that give a rather dark red appearance, the distinctive coloring corresponding approximately to the following in Maerz & Paul's Dictionary of Color (1930): Gladioulus Color, Plate 2, K 5; highlighted with Coral Red, Plate 2, J 10; shaded with Pompeian Red, Plate 4, J 10.

The outer skin of the fruit is generally of Pinard Yellow, shaded with Empire Yellow, as seen, respectively, in Plate IV, 21, *d*, and Plate IV, 21, *b*, of Robert Ridgway's Color Standards and Nomenclature.

We have reproduced our variety of grapefruit tree, true in every detail to all of the color and other characteristics of the fruit discovered by us in the above mentioned grove, by budding from the sport found by us.

The first fruit, from trees thus reproduced and grown by us, was picked during the harvesting season of 1947–1948, we have continued to bud nursery stock of this variety, and all fruit of that stock continues to be true in color and other characteristics to the fruit budded from the original sport discovered by us.

The distinctive coloring of the fruit flesh is present by the time the fruit is the size of a standard golf ball or smaller, and the coloring remains permanent and does not begin to fade, as do other colored flesh grapefruit, as soon as maturity is reached; that is, the coloring is permanent from shortly after the fruit begins development from the blossoms through the normal time of reaching the consumer. The coloring does not blend into the rind of the fruit, but it is retained in the flesh, juice cells, and the partitions of the fruit.

The Thompson pink, unpatented, and the Ruby Red grapefruit mentioned in the Henninger Plant Patent No. 53 begin to fade as soon as they have reached the maturity stage. Our fruit has been under observation for over four years, it has retained its coloring of flesh as long as it remained on the tree, and thereafter during the normal time required to reach the consumer. The red coloring pervades throughout the flesh, rather than in border as with the Henninger fruit.

Aside from permanence of flesh coloring, it has been found that our fruit has superior keeping qualities from the time it is picked and during the period usually required to reach the table of the retail purchaser. For example, specimens of our fruit and of other flesh-colored grapefruit were picked at the same time, and all kept together in the conditions to which grapefruit normally is subjected in its progress from the tree to the consumer. At the end of about a month and a half, it was found that our variety of grapefruit was plump and showed no evidence of shriveling or other deterioration, whereas the other fruit of the lot tested had started to shrivel and the flesh had faded.

Our variety of grapefruit has not been introduced to the trade or marketed as a distinct variety up to the time of this application.

Other characteristics of our new and distinct variety are:

*Fruit*

*Form.*—Oblate-rounded, and generally uniform in shape in the several sizes.

*Size.*—Mature fruit varies, but is of substantially uniform proportions, and sizes usually found in grapefruit; for example: about 3⅛ inches in depth by 4⅞ inches in diameter; 3½ inches in depth by 4½ inches in diameter, when measuring specimens taken at random.

*Rind.*—Normally about ⅛ inch thick.

*Oil cells.*—Small, scarcely or not at all indented.

*Segments.*—Normally 13, uniform, partitions thin.

*Juice sacs.*—Small, juice abundant.

*Flavor.*—Delicious; bitter principle not strongly marked; acidity and sweetness medium and well blended.

*Pith.*—Normally about ⅝ inch in diameter; open.

*Seeds.*—2 to 6, or none; large, plump.

*Season.*—November through August.

*Tree*

The tree upon which our variety of grapefruit is produced is similar in appearance as to tree type, leaf growth, method of blooming, and some other observable characteristics to corresponding features of the pink Marsh grapefruit trees that have been cultivated and grown commercially. Technically it may be described as follows:

*Tree.*—Round topped, with dense foliage. Has many strong, widely branched, scaffold limbs. Rarely exceeds 25 feet in total height.

*Twigs.*—Angular when young, glabrous or nearly so, robust and strong growing and not notably spinney.

*Leaves.*—Larger than sweet orange and smaller than pummelo; occur singly; bluntly tipped, and broadly rounded at base; tending glabrous. Petioles are broadly winged, but not so broad as pummelo; obovate or oblanceolate in shape. The somewhat broadly rounded tip of the petiole touches the somewhat broadly rounded base of the leaf blade. Mature leaves are dark green of dense texture, with fine scattered oil cells showing through.

*Flowers.*—Large and borne singly or in small clusters; do not possess color characteristics such as occasionally are found in pummelo and lemons.

We claim:

A new and distinct variety of grapefruit tree characterized as to novelty by fruit having flesh of rather dark red appearance produced by presence of several reddish pervading hues, permanence of the coloring through development of the fruit to maturity and to usual time of consumption, and the long keeping qualities of the fruit.

No references cited.